United States Patent [19]

Bryant et al.

[11] Patent Number: 5,738,657
[45] Date of Patent: Apr. 14, 1998

[54] AMBULATORY ENERGIZED CONTAINER SYSTEM

[75] Inventors: Peter L. Bryant, Libertyville; Nicolaos A. Drivas, Des Plaines; Rodney M. Mittag; John K. Moore, both of Highland Park; Edward S. Tripp, Antioch; William L. Rudzena, McHenry, all of Ill.; John C. Williams, Union Grove, Wis.

[73] Assignee: Abbott Laboratories, Abbott Park, Ill.

[21] Appl. No.: 769,822

[22] Filed: Dec. 19, 1996

Related U.S. Application Data

[63] Continuation of Ser. No. 331,583, filed as PCT/US93/05736, Jun. 15, 1993, published as WO93/25269, Dec. 23, 1993, abandoned, which is a continuation-in-part of Ser. No. 898,259, Jun. 15, 1992, abandoned.

[51] Int. Cl.⁶ ............................................. A61M 37/00
[52] U.S. Cl. ............................ 604/145; 604/140; 222/95
[58] Field of Search ............................... 604/403, 408, 604/410, 411, 140, 141, 145, 122; 441/98–101, 30, 31; 222/95

[56] References Cited

U.S. PATENT DOCUMENTS

| | | |
|---|---|---|
| 1,633,608 | 6/1927 | Sartakoff . |
| 2,766,907 | 10/1956 | Wallace . |
| 3,023,750 | 3/1962 | Baron . |
| 3,469,578 | 9/1969 | Bierman . |
| 3,847,149 | 11/1974 | Murray et al. . |
| 4,267,834 | 5/1981 | Barger et al. . |
| 4,369,578 | 1/1983 | Ernst . |
| 4,379,453 | 4/1983 | Baron ........................ 604/145 |
| 4,447,230 | 5/1984 | Gula et al. ................. 604/122 |
| 4,460,365 | 7/1984 | Ganshirt et al. ........... 604/408 |
| 4,468,220 | 8/1984 | Willbanks . |
| 4,507,116 | 3/1985 | Leibinsohn . |
| 4,626,243 | 12/1986 | Singh et al. . |
| 4,718,430 | 1/1988 | Holzer . |
| 4,735,613 | 4/1988 | Bellin et al. . |
| 4,739,770 | 4/1988 | Stephens et al. . |
| 4,929,214 | 5/1990 | Liebermann ............... 441/31 |
| 4,947,856 | 8/1990 | Beard ......................... 128/673 |
| 5,053,011 | 10/1991 | Strobel et al. . |
| 5,059,182 | 10/1991 | Laing . |

FOREIGN PATENT DOCUMENTS 2041756  1/1980  United Kingdom .

*Primary Examiner*—John G. Weiss
*Assistant Examiner*—Dennis Ruhl
*Attorney, Agent, or Firm*—Brian R. Woodworth

[57] ABSTRACT

An ambulatory infusion and/or KVO (keep vein open) system (12, 18) has a gas-pressurized bladder arrangement (12) including a gas barrier associated therewith. The system includes a flexible bag of solution (13) inserted in a sleeve portion (36) of the bladder arrangement (12). Internal gas pressure which is developed within the bladder arrangement by a selectively initiated chemical reaction exerts a continuing pressure against the solution bag (13) to cause the solution to flow therefrom. A tubing set (18) of the system includes a flow restrictor (24) which is sized for minimal flow rates for indwelling catheter patency maintenance.

9 Claims, 10 Drawing Sheets

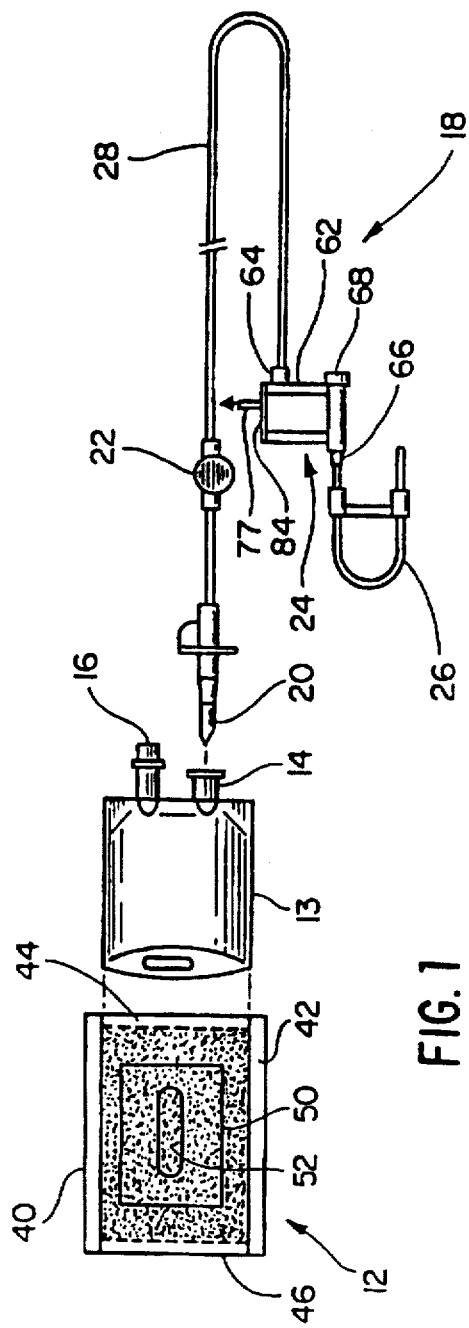
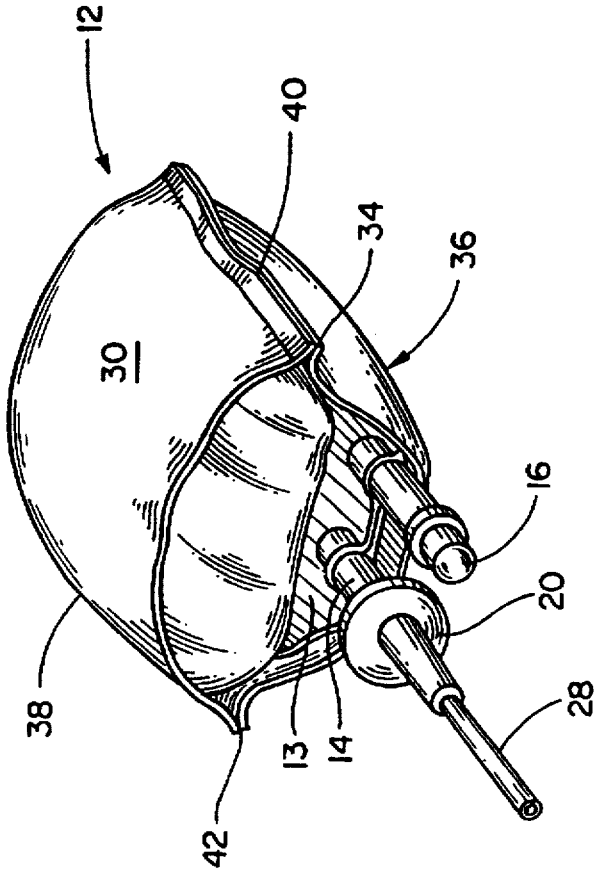

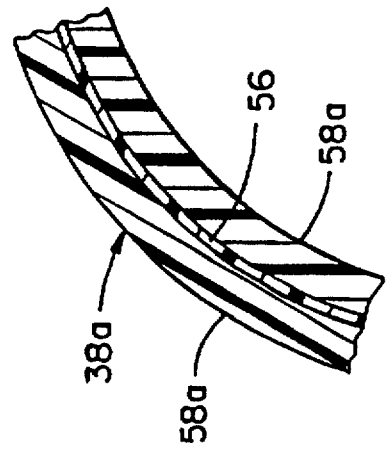
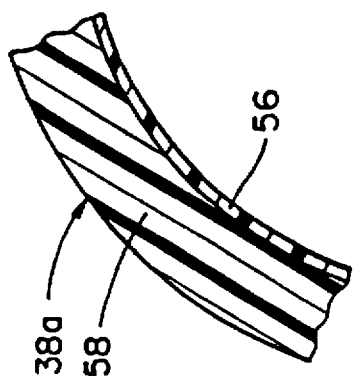
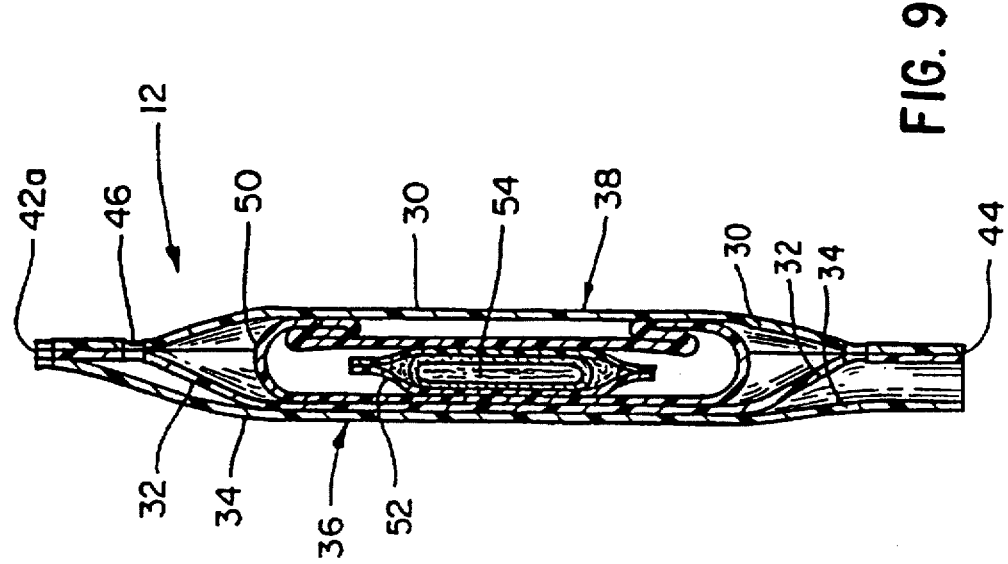

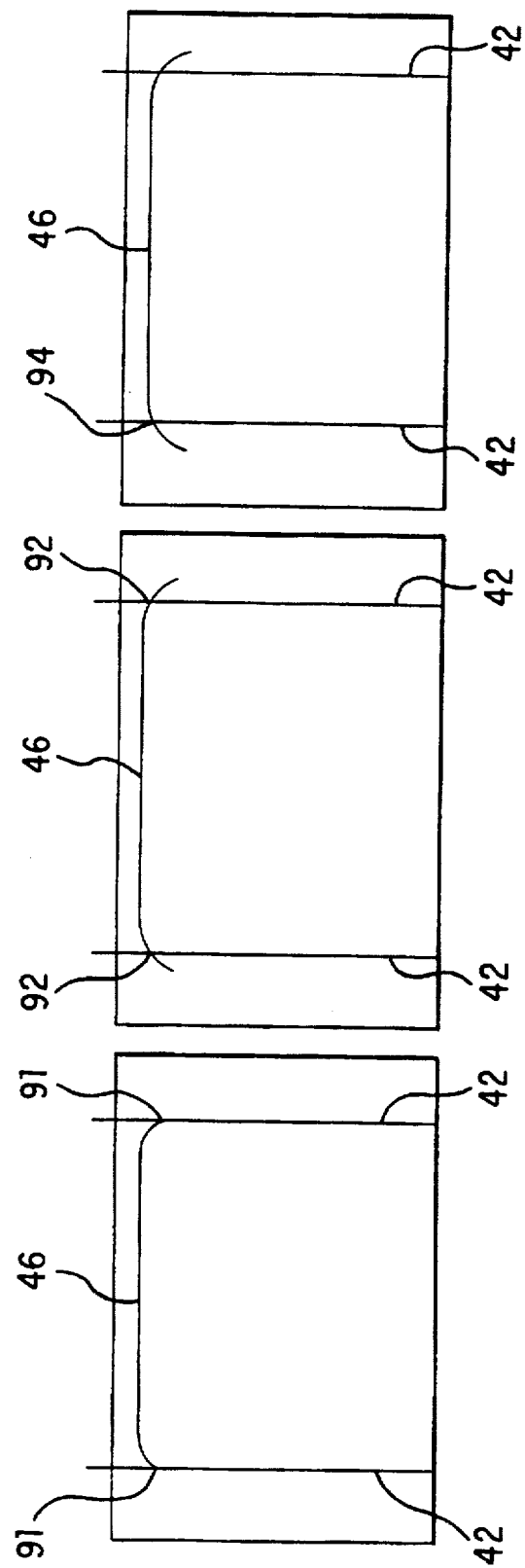

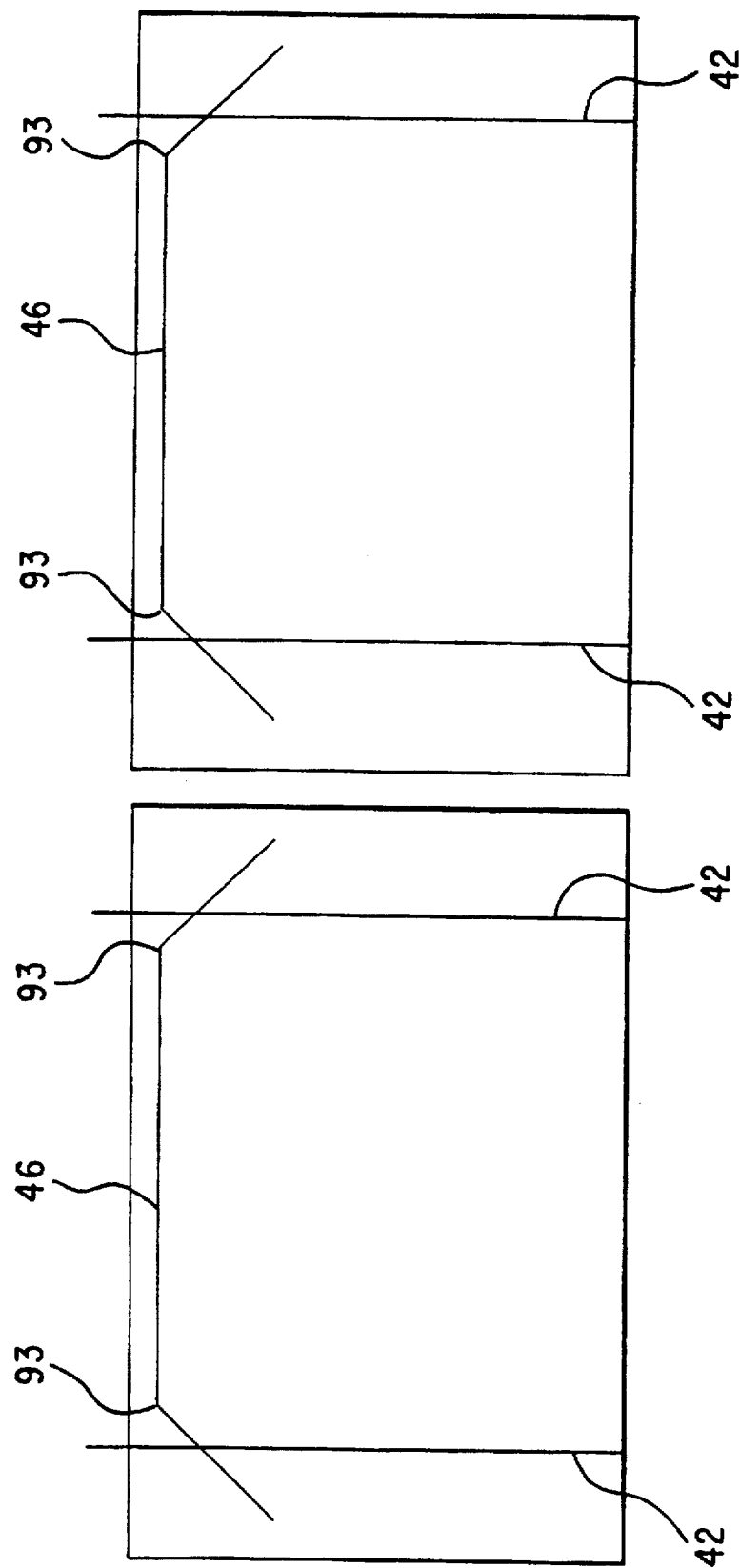

AMBULATORY ENERGIZED CONTAINER SYSTEM

This application is a continuation of application Ser. No. 08/331,583, filed Nov. 2, 1994, now abandoned, which is a 371 of PCT/US93/05736, filed Jun. 15, 1993, published as WO93/25269 Dec. 23, 1993, which is a continuation-in-part of application Ser. No. 07/898,259, filed Jun. 15, 1992 now abandoned.

BACKGROUND OF THE INVENTION

There are many patients on intermittent I.V. medication who are healthy enough to be more freely ambulatory if it were not necessary for them to be tied down to a hospital or clinic so that patency in their venipuncture sites could be maintained by means of a standard in-hospital KVO (keep vein open) therapy or lengthy, relatively involved heparin or saline lock therapies requiring flushing of the patient's venipuncture site before and after each administration of medication, which therapies are relatively costly and result in a large volume of waste to be disposed of. Although some ambulatory KVO therapies have been tried, none have been able to successfully maintain the necessary positive pressure, continuous fluid flow patency for a long enough period to make their use worthwhile.

An object of the invention is to provide a new ambulatory energized container KVO system which is effective for an advantageous period of time.

Another object of the invention is to provide a new ambulatory self-energized KVO system which is lightweight and which is disposable in its entirety after being used.

A further object of the invention is to provide a new ambulatory energized container system having a combination bladder and sleeve member which while being flexible, maintains an enhanced degree of structural integrity while being pressurized for an extended period of time, for example for greater than 48 hours.

An additional object of the invention is to provide a new design for construction of a new combination sleeve and bladder member of an energized container system of the invention, which design is advantageously forgiving of deviations from manufacturing specifications during lamination procedures involved in construction of the combination sleeve and bladder member.

Other objects of the invention will become apparent to the reader infra.

SUMMARY OF THE INVENTION

The present invention is for an ambulatory energized container system suitable for developing a continuous pressure on, and flow of, a solution from a flexible bag for solution into a patient's indwelling vein access device, for example sufficient for keeping the patient's vein open even though medication may be administered through the access device only intermittently. The ambulatory energized container system comprises a combination sleeve and bladder member (combination member). The combination member has a bladder portion and a sleeve portion. A flexible bag for solution can be inserted into the sleeve portion. The flexible bag for the solution has an outlet port suitable for connection to a tube set connectable between the outlet port of the bag and the patient's vein access device. The flexible bag for solution optionally may be associated with said sleeve portion so as to be essentially or completely non-removable therefrom.

The bladder portion of the combination member is made of a flexible plastic material, for example a multilayer laminated material, and is expandable upon introduction of a gas into the bladder portion. The sleeve portion of the combination member is made of a flexible material, for example a multilayer laminated material. The sleeve portion is designed to receive therein, or to have integrally associated therewith, the flexible bag for solution in a position in the sleeve portion alongside the bladder portion of the combination member such that upon expansion of the bladder portion upon introduction of gas into the bladder portion, continuous pressure is applied through the sleeve portion to the flexible bag for solution when the bag has solution therein.

The bladder portion of the combination member also has associated with it barrier means for containing liquid and gas. Gas-generating, reactive, chemical means are disposed within the barrier means in an ambulatory energized container system of the invention. Additionally, the ambulatory energized container system includes segregating means for segregating reactive components of the gas-generating reactive chemical means, for example two reactive chemical compounds, from one another prior to chemical reaction. Activation of an ambulatory energized container system of the invention involves removal of the segregating means, for example by manual manipulation or breaking at least a portion thereof, which results in a chemical reaction and the formation of a volume of gas sufficient to expand the bladder portion thereby exerting a continuing pressure on the flexible bag for solution inserted in the sleeve member (or integral with the sleeve member), the bag having solution therein.

The barrier means for containing liquid and gas can comprise a first sealed expandable barrier container which is permeable to gas and which contains the gas-generating reactive chemical means. This first barrier container is disposed within the bladder portion of the combination member and typically serves to contain moisture and debris formed during reaction of the gas-generating chemical means.

The barrier means for containing liquid and gas may also comprise a second sealed expandable barrier container which is substantially gas-impermeable. For example, such a second sealed expandable barrier container may be employed in embodiments of the invention wherein the walls of the bladder portion itself are not designed to contain a pressurized gas inside the bladder portion over an extended period of time, for example for at least 48 hours, and such containment is desired for a particular patient procedure. However, such a second sealed expandable barrier container can be dispensed with, for example, where the walls of the bladder portion themselves are designed to be substantially or essentially gas-impermeable or where the period of time for which the pressure of a gas in the bladder portion needs to be maintained does not have to be very long, for example under two hours.

Another aspect of the invention involves flexible plastic materials which may be utilized for the bladder portion of the combination member and for part or all of the sleeve portion of the combination member. In one aspect, the flexible plastic material of the walls of the bladder portion comprises at least two laminated layers (of plastic material) of differing material stiffness wherein the layers are arranged, looking in a direction outwardly from the interior of the bladder portion, in order of decreasing material stiffness. In other words, the layer of the composite laminate having the greatest material stiffness (or highest elastic modulus) lies closest to the interior of the bladder portion. Likewise, at least for the wall of the sleeve portion which also serves as a wall of the bladder portion, wherein the flexible material of the sleeve portion comprises at least two laminated layers (of plastic material) of differing material stiffness, the layers are arranged, again looking in a direction outwardly from the interior of the bladder portion, in order of decreasing material stiffness. Thus, the layer of the composite laminate of at least the wall of the sleeve portion lying closest to the interior of the bladder portion has the greatest material stiffness (or highest elastic modulus).

BRIEF DESCRIPTION OF THE DRAWINGS

Additional objects and advantages of the present invention will become apparent when taken in connection with the accompanying drawings, in which:

FIG. 1 is a diagrammatic, exploded view of an ambulatory energized container KVO system illustrating a preferred embodiment of the invention;

FIG. 2 is a perspective view of the combination sleeve and bladder member of the system of FIG. 1 after insertion of a flexible bag of saline solution to be infused into the sleeve portion of the combination sleeve and bladder member, after spiking of the outlet port, and after pressurization of the bladder portion;

FIG. 9 is a vertical sectional view through the combination sleeve and bladder member and taken generally along line 9—9 of FIG. 8;

FIG. 10 is an enlarged fragmentary sectional view taken through a second embodiment of the bladder member wherein the barrier means is laminated or coated to the inner surface thereof;

FIG. 11 is an enlarged fragmentary sectional view similar to FIG. 10 but taken through a third embodiment of the bladder member wherein the barrier means is embedded therein;

FIG. 13 shows in schematic form optimal placement of seal bars for making side-edge welds in relation to a top weld during lamination to form a combination sleeve and bladder member;

FIG. 14 shows in schematic form placement of seal bars for making side-edge welds in relation to a top weld during lamination to form a combination sleeve and bladder member to produce side-edge welds which cross the midpoints of the corner curves from a top weld;

FIG. 15 shows in schematic form placement of seal bars for making side-edge welds in relation to a top weld during lamination to form a combination sleeve and bladder member which placement results in a 90 degree angle at one of the corners;

FIG. 16 shows in schematic form a placement of seal bars for making side-edge welds in relation to a top weld during lamination to form a combination sleeve and bladder member in which placement results in equal cross over angles at both sides as a result of employing 45 degree angles at the side-most portions of the top seals; and FIG. 17 is similar to FIG. 16 except that the seal bars for making the side-edge welds in relation to a top weld have been shifted to the right.

DETAILED DESCRIPTION OF THE INVENTION

Figure 3:
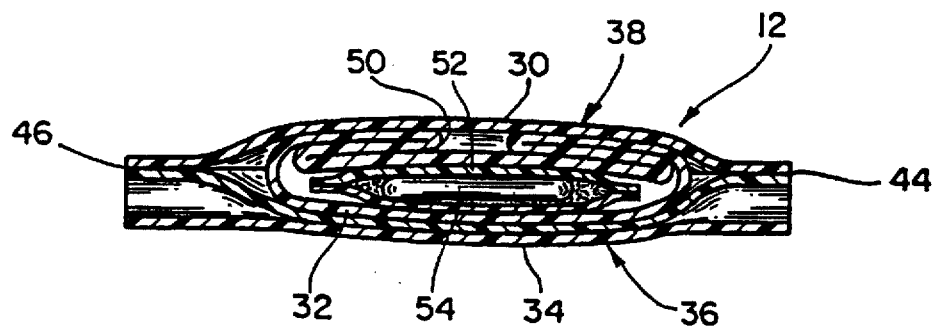
FIG. 3 is a longitudinal section taken through the deflated sleeve and bladder member, including the separate barrier means sealed therein, prior to insertion of a flexible bag of saline solution into the sleeve portion thereof and prior to pressurization of the bladder portion thereof.

The new and improved ambulatory energized container KVO system is effective for an advantageous period of time. The energized container system of the invention is characterized by a chemically pressurized bladder which exerts a continuing pressure on a flexible bag of solution to be administered to a patient, for example saline solution, to force the solution therefrom through a restrictor at a resulting low rate through the patient's indwelling vein access device to maintain patency of the vein access site, the pressure of the solution at the site being slightly greater than the pressure within the vein. The restrictor has associated therewith a reseal for administering medication to the patient intermittently and a manually operable bypass for easily flushing the reseal, restrictor and vein access device after each administration of medication.

The bladder portion of the combination bladder and sleeve member is made of a flexible plastic material, for example a multilayer laminated material, and is expandable upon introduction of a gas into the bladder portion. The bladder can be formed of a relatively tough plastic such as polyurethane, polyvinylidene chloride, fabric reinforced polyurethane, shore 90A durometer material and the like and combinations thereof. These materials are somewhat permeable to the pressurized gas formed therein but are adequate for use in those applications having a short term usage. When an application requires a longer duration, gas barrier means, which is relatively impermeable to the pressurized gas, is associated with the bladder whereupon the bladder is able to sustain its pressure against the bag of solution for at least forty-eight hours.

Such gas barrier means may be in the form of a separate sealed balloon, a barrier film laminated to the bladder portion itself, or a coating on the bladder portion. A further gas-permeable, moisture-and-debris barrier means, for example in the form of a sealed packet, is provided within the bladder with normally segregated reactive chemicals being disposed therein. Suggested chemicals are loose sodium bicarbonate and a frangible vial of citric acid which is readily breakable by manual manipulation through the flexible bladder and moisture-and-debris barrier means to initiate the chemical reaction and pressurize the bladder portion by the formation of a gas such as carbon dioxide.

The flexible bag of solution to be infused, for example saline solution, for this ambulatory energized KVO system is inserted into the sleeve portion of the combination sleeve and bladder member in side-by-side relationship therewith, the sleeve and bladder member being attachable to the patient's wearing apparel, whether a hospital gown or street clothes. The sleeve and bladder member is also provided with an "EMPTY" indicator.

The new and improved ambulatory self-energized KVO system of the invention is lightweight and, in its entirety, is disposable after being used.

In one aspect of the invention, the new and improved energized container system is characterized by a sleeve and bladder member, with the sleeve portion being adapted to receive (or having integrally associated therewith) a bag for solution such as saline solution to be continuously infused at a minimal flow rate and with the bladder portion adapted to be pressurized by a selectively initiated chemical reaction therein, and by a tube set including an air filter and a restrictor having a reseal for intermittent medication ads and a bypass for flushing thereafter.

In another aspect of the invention, the bladder portion provides a high volume, high pressure gas reservoir, and maintains a nearly constant pressure on the flexible bag of solution during up to a two hour period or longer in which the solution is being delivered to the patient.

In another aspect of the invention, the bladder portion, which provides a high volume, high pressure gas reservoir, is characterized by a rugged, expandable outer plastic film and by an inner, sealed, gas impermeable balloon, which bladder portion maintains a nearly constant pressure on the flexible bag of solution such as saline during at least a forty-eight hour period during which the solution is being delivered to the patient.

In another aspect of the invention, the bladder portion has a gas barrier lamination or coating associated therewith.

In another aspect of the invention, the new and improved energized container system is small enough and light enough to be attached to a patient's clothing and has an "EMPTY" indicator provided on the sleeve and bladder member.

Referring now to the drawings, as illustrated in FIG. 1, one embodiment of the invention includes a combination sleeve and bladder member 12 which is formed of a relatively rugged and tough plastic film material which is flexible, expandable and has a relatively high tensile strength, such as polyurethane, JPS Elastomerics, MP-890, with a thickness of 20 mil and a durometer of Shore 90A. The ambulatory, self-energized container KVO (keep vein open) infusion system of the invention also includes a flexible bag 13 of solution, such as saline solution, which is to be infused at a continuous minimal flow rate into a patient through an indwelling vein access device, such as a catheter (not shown), to permit the administration of medication intermittently. This continuous low rate of infusion at a positive pressure slightly greater than the pressure within the vein maintains the patency of the access site between medication administrations and also prevents any back flow of blood into the system. This system is designed to be effective over a period of forty-eight hours or more with the bag 13 of saline solution having a volume of only 100 ml. The bag 13 is provided with an outlet port 14. Although the bag 13 is shown in FIGS. 1 and 2 is also shown with a reseal port 16 for making additives to the contents of the sealed bag 13, this reseal port is nor a necessary element of this KVO infusion system, the outlet port 14 being all that is necessary. As shown, the system further includes a tube set 18 having a pin 20 for spiking the outlet port 14 of the bag 13 of saline solution, an air elimination sterilizing filter 22, such as a 0.2 micron FILTERTEK filter, a low flow capillary restrictor 24 (to be described in greater detail hereinafter), a J-loop 26 for connection to the patient's indwelling vein access device (catheter), suitable lengths of interconnecting plastic tubing 28, such as 0.043×0.138 size tubing, and suitable connectors, as needed.

Figure 8:
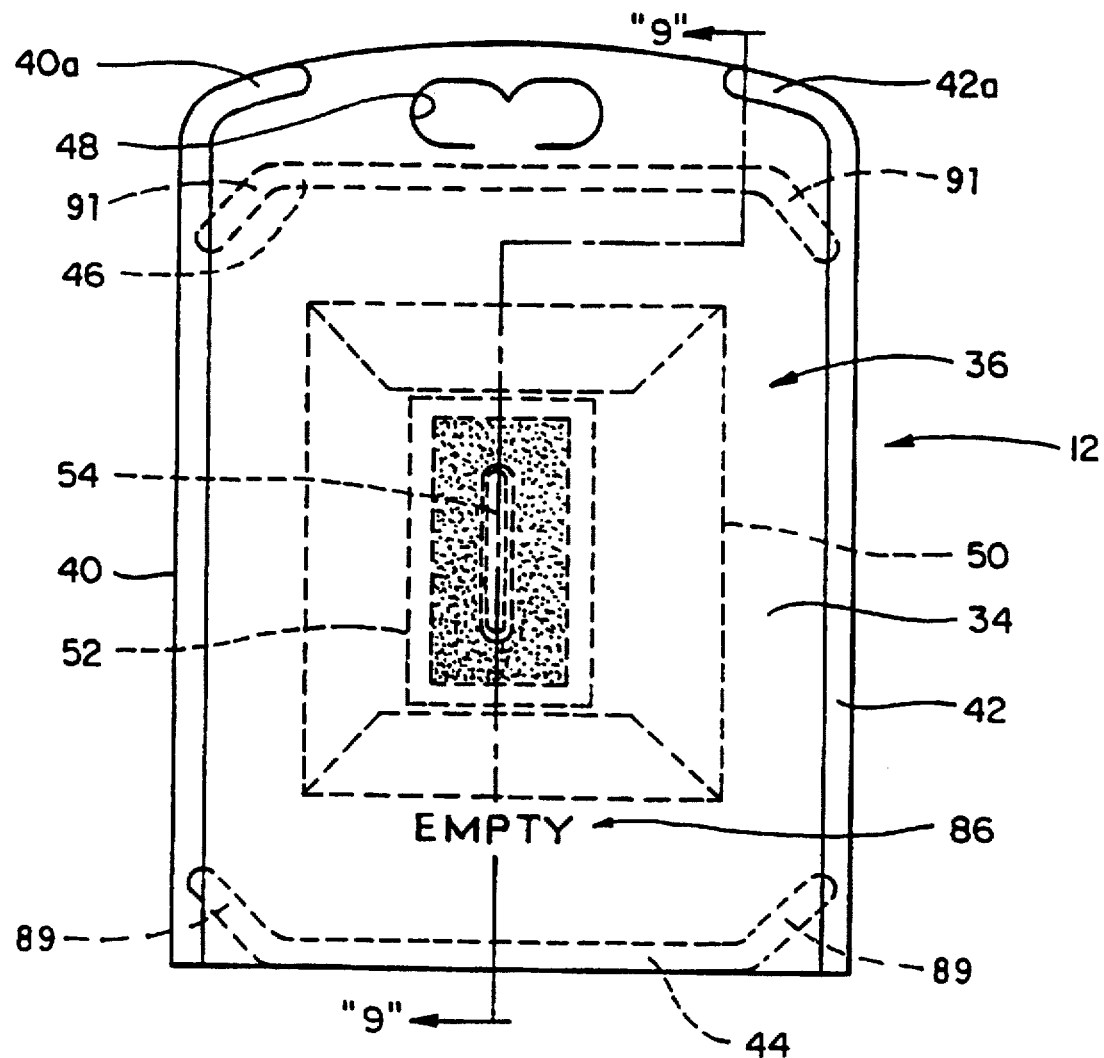
FIG. 8 is an enlarged front elevational view of the deflated combination sleeve and bladder member prior to insertion of a flexible bag of saline solution in the sleeve portion thereof and prior to pressurization of the bladder portion thereof.

As best illustrated in FIGS. 8 and 9, the combination sleeve and bladder member 12 is formed by three generally rectangular sheets 30, 32 and 34 of plastic, such as polyurethane or polyurethane-coated fabric, which overlie one another and are sealed together, as by welding, in a manner to be described hereinafter, to provide a sleeve portion 36 and a bladder portion 38. The side edges of all three sheets 30, 32 and 34 are welded (sealed) together, as at 40 and 42 in FIG. 8 to form two three-layer welds (seals), with the welds (seals) extending inwardly from each edge of the member 12 a distance approximately equal to one-quarter of the width thereof, as at 40a and 42a, for a purpose which will be made clear hereinafter. Prior to the foregoing side-edge welding of all three sheets 30, 32 and 34, the two adjacent sheets 30 and 32 are welded together at their bottom edges, as a 44 in FIGS. 8 and 9, and along their upper portions spaced a relatively short distance below the upper edges thereof, as at 46 in FIGS. 8 and 9 to form two two-layer welds (seals), whereby sheets 30 and 32 define the four-sided sealed bladder portion 38 with sheet 30 serving as the outer side wall thereof and sheet 32 serving as the inner side wall thereof and whereby sheets 32 and 34 define the sleeve portion 36 which is partially sealed at its upper end and fully open at its lower end with sheet 34 serving as the outer side wall of the sleeve portion 36 and sheet 32 serving double-duty as the inner side wall thereof as well as the inner side wall of the bladder portion 38. As illustrated, the four outer ends 89 and 91 of the two first-step bladder welds 44 and 46, respectively, are inclined inwardly, preferably at a 45 degree angle from the remaining horizontal portion of the welds, toward the center of the sleeve and bladder member 12 and into sealed engagement with the two second-step side welds 40 and 42. An opening 48 for attaching any one of a number of known hangers is provided in the upper edges of sheets 30 and 32, at the center thereof, so that the sleeve and bladder member 12 may be readily attached to a patient's clothing, be it a hospital gown or street wear.

Thus as illustrated in FIGS. 8 and 9 axed discussed in detail above, the combination sleeve and bladder member 12 is formed by three generally rectangular overlying sheets 30, 32 and 34 of plastic with the side edges of all three sheets being sealed together to form two three-layer seals (welds) and with two adjacent sheets 30 and 32 of the three sheets being sealed together along the bottom edges thereof (as at 44) and along the upper portions thereof (as at 46) spaced below the upper edges thereof to form two two-layer seals (welds). Each of the two-layer seals (welds) extends outwardly (as at 89 and 91) from each of the bottom edges and upper portions of the two adjacent sheets toward each of the side edges of the two adjacent sheets at essentially, preferably exactly, 45 degree angles from the remaining horizontal portions of the two-layer seals (welds). The resulting combination sleeve and bladder member 12 has a sealed bladder portion 38 of the combination member 12, the sleeve portion 36 of the combination member 12 being defined by the two adjacent sheets which are not sealed together at their tops and bottoms, the middle of the three sheets defining both an inner side wall 32 of the sleeve portion 36 and an inner side wall 32 of the bladder portion 38, the sleeve and bladder portions being disposed in side-by-side relationship.

It has been found that because the bladder portion of the combination member becomes inflated, stress on the seal area and the film will be less the closer the inflated system is to a sphere. But having a rectangular shape before inflation produces high stress areas in the corners which is not desirable. Rounding the corners as illustrated in FIGS. 13, 14 and 15 relieves the excessive stress upon inflation of the bladder portion; however, it creates problems with consistency of manufacturing as can be seen from considering FIGS. 13, 14 and 15. As can be appreciated from considering FIG. 13, placing the side-edge welds 42 at the optimal points 91 for reducing stress results in a design that allows no clearance or latitude for deviation from perfect alignment of the side-edge seals 42. If the unit to be laminated shifts to the left or right when positioned in a die for forming the side-edge seals 42, the seals will not overlap with both of the top and bottom seals (top only shown) and an open bladder will be produced. As can be appreciated from FIG. 14, by targeting the side-edge seals (welds) at the midpoints 92 of the corner curves, the stress can be minimized since the incidence angles at these points are 45 degrees. However, as can be appreciated from FIG. 15, as normal manufacturing variations occur, an incident angle can approach a 90 degree angle (shown at 94 on left side of FIG. 15) and therefore provide no benefit over a straight seal bar.

Benefits of the discovery of the invention of an improved configuration for the corner seals (the 45 degree angle configuration) can be appreciated from FIGS. 16 and 17. A 45 degree angle (or 45 degree chamber), shown at 93 in FIGS. 16 and 17, is preferred from the standpoint of reducing stress on the corner seals. Utilization of a 45 degree angle (chamber) eliminates the variability due to movement of the film sheets, to be laminated together, below the manufacturing dies. FIG. 16 shows the die cross-over at the nominal design placement. The angles made by the top die crossing both of the chambers are both 45 degrees. From FIG. 17 it can be seen that as the alignment changes as part of normal manufacturing process variation, both angles remain constant at 45 degrees thereby minimizing stress upon inflation of the resulting bladder portion. Additionally, this configuration of the corner seals results in minimal variation in volume of the bladder portion from unit to unit that occurs from the position in FIG. 16 to the position in FIG. 17.

Figure 4:
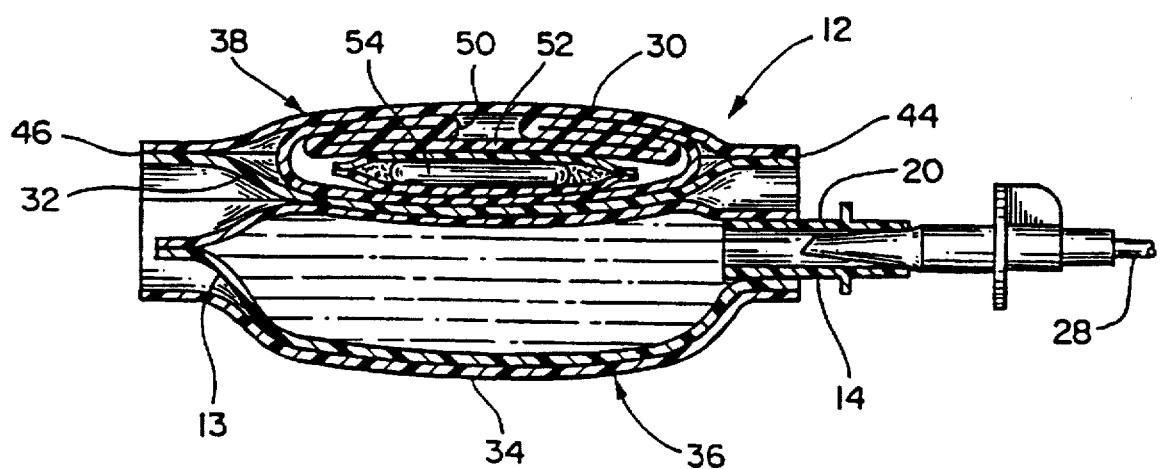
FIG. 4 is a longitudinal section similar to FIG. 3 after insertion of a flexible bag of saline solution into the sleeve portion of the deflated sleeve and bladder member, also prior to pressurization thereof.
Figure 5:
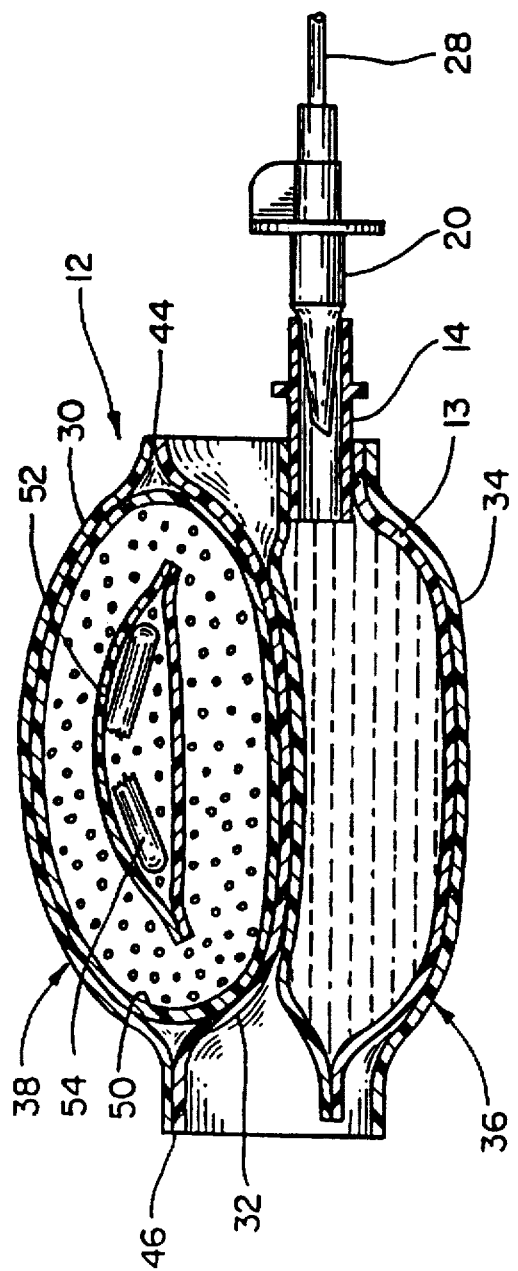
FIG. 5 is a longitudinal section similar to FIGS. 3 and 4 after pressurization of the bladder portion of the sleeve and bladder member.
Figure 5A:
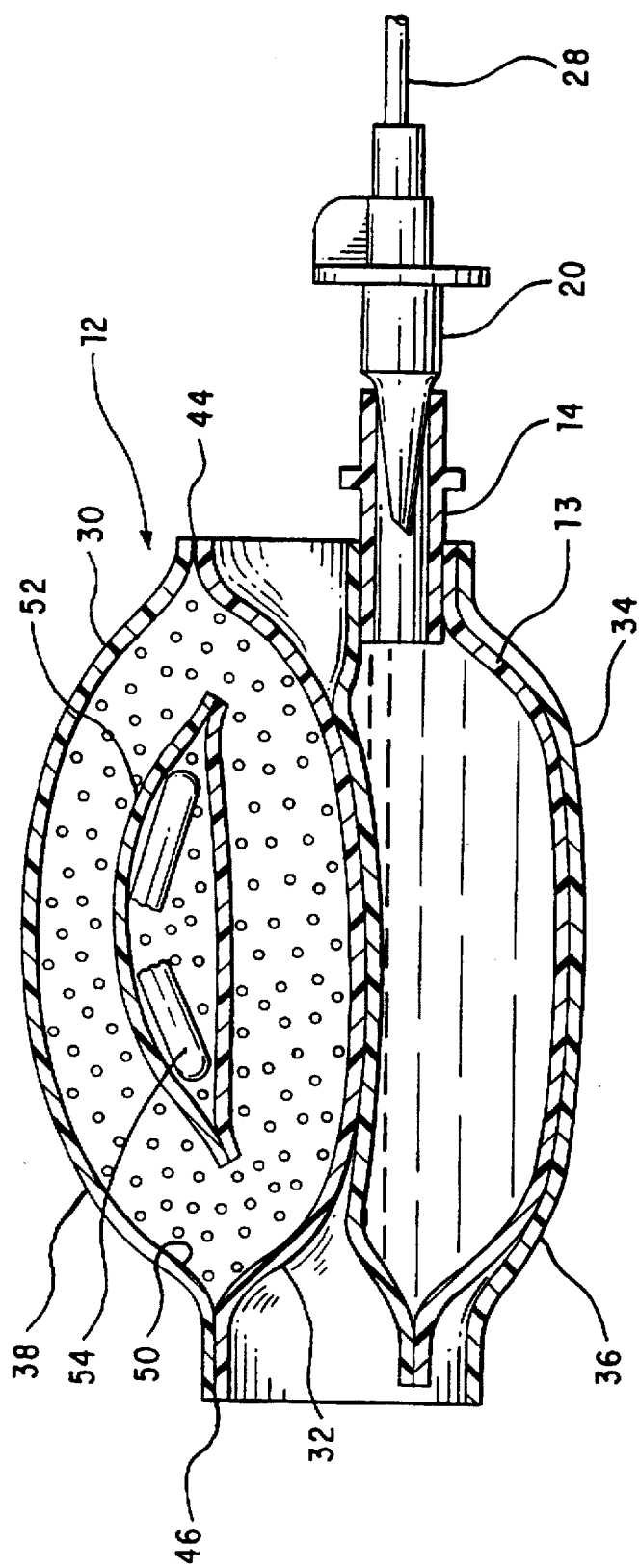
FIG. 5A is a longitudinal section similar to FIG. 5, but excluding the separate barrier means sealed within the bladder portion of the sleeve and bladder member.

The sleeve portion 36 of the combination member 12 is of a size to receive the 100 cc flexible bag 13 of saline solution when inserted therein from the bottom whereupon the bag 13 is disposed in side-by-side relationship with the bladder portion 38, as shown in FIG. 4, prior to pressurization thereof. As shown, after this insertion of the bag 13 from the bottom, the outlet port 14 thereon depends from the sleeve and bladder member 12 and is readily accessible for spiking of same. Insertion of the bag 13 from the top of the sleeve and bladder member 10 is prevented by the inwardly directed weld extensions 40a and 42a.

As will be more fully described hereinafter, the bladder portion 38 is to be pressurized so that it defines a high volume, high pressure gas reservoir which is adapted to exert a continuing pressure on the bag 13 of saline solution so as to infuse the 100 cc's of solution into a patient over a given period. As most plastic films under such high pressures will lose pressure due to their innate gas-permeability, particularly over a period as long as forty-eight hours, it has been determined that for an energized container system of the invention intended for use over such an extended period, e.g., for more than 48 hours, highly impermeable gas barrier means should be associated with the bladder portion 38, either as a separate element, as a laminate, or as a coating to provide an effective solution to this problem by preventing gas permeation and by maintaining adequate pressurization.

Just one example of such gas-impermeable barrier means is illustrated in FIGS. 2–5, 8 and 9. This barrier means is in the form of a sealed balloon 50 which is initially deflated, folded and sealed within the bladder portion 38 and which is formed of a 3 mil film of polyvinylidene chloride, for example available commercially from Dow Chemical as Saranex 15. A further gas-permeable, moisture-and-debris barrier means, in the form of a sealed, folded packet 52 formed of a non-woven polypropylene fiber material, for example available commercially as Tyvek, is sealed within the balloon 50. Disposed within the packet 52 are reactive chemicals such as sodium bicarbonate and citric acid, which chemicals are normally segregated for example by encasing the citric acid in a frangible ampoule 54. To provide the necessary volume of highly pressurized gas such as carbon dioxide, 4¼ grams of loose sodium bicarbonate are provided in the packet 52 and 2½ cc.'s of 50% citric acid are provided in the ampoule 54, per 350 cc's of bladder volume. As the amount of citric acid controls the volume of gas generated, excess sodium bicarbonate may be present in the packet 52 and such excess is desirable. When it is time to energize the bladder portion 38, the ampoule 54 may easily be broken by manually manipulating same through the flexible bladder portion 38, the balloon 50, and the packet 52. The packet 52, which is permeable to the carbon dioxide gas formed by the chemical reaction following breaking of the ampoule 54, serves as a barrier to contain most of the moisture and debris such as other by-products of the chemical reaction and all fragments of the ampoule 54 which could have sharp edges. The volume of gas formed passes through the packet 52 and inflates the balloon 50 which then physically expands the flexible bladder portion 38 which, in turn, exerts a continuing pressure on the flexible bag 13 of saline solution.

An alternative embodiment of barrier means for the bladder portion 38 constitutes a laminated or coated bladder portion 38a wherein a 1 mil sheet 56 or coating of polyvinylidene chloride, commercially known as Saran, is laminated or coated to 20 mil of polyurethane, in either of two forms. As illustrated in FIG. 10, the layer 56 of polyvinylidene chloride is laminated to the inner surface of a 20 mil layer 58 of polyurethane whereas in FIG. 11 the 1 mil layer 56 of polyvinylidene chloride is laminated and embedded between two 10 mil layers 58a of polyurethane. In each embodiment, the layer 56 of polyvinylidene chloride serves as the impermeable gas barrier. With either of the latter two embodiments (FIGS. 10 and 11) wherein the separate gas barrier balloon 50 is eliminated, it is noted that only the two bladder-defining sheets 30 and 32 need be laminated with the layer 56 of polyvinylidene chloride. The other sleeve-defining sheet 34 may comprise, for example, a single layer of polyurethane. However, in both of the latter two embodiments (FIGS. 10 and 11), the barrier packet 52 is still sealed within the bladder portion 38a.

Figure 12:
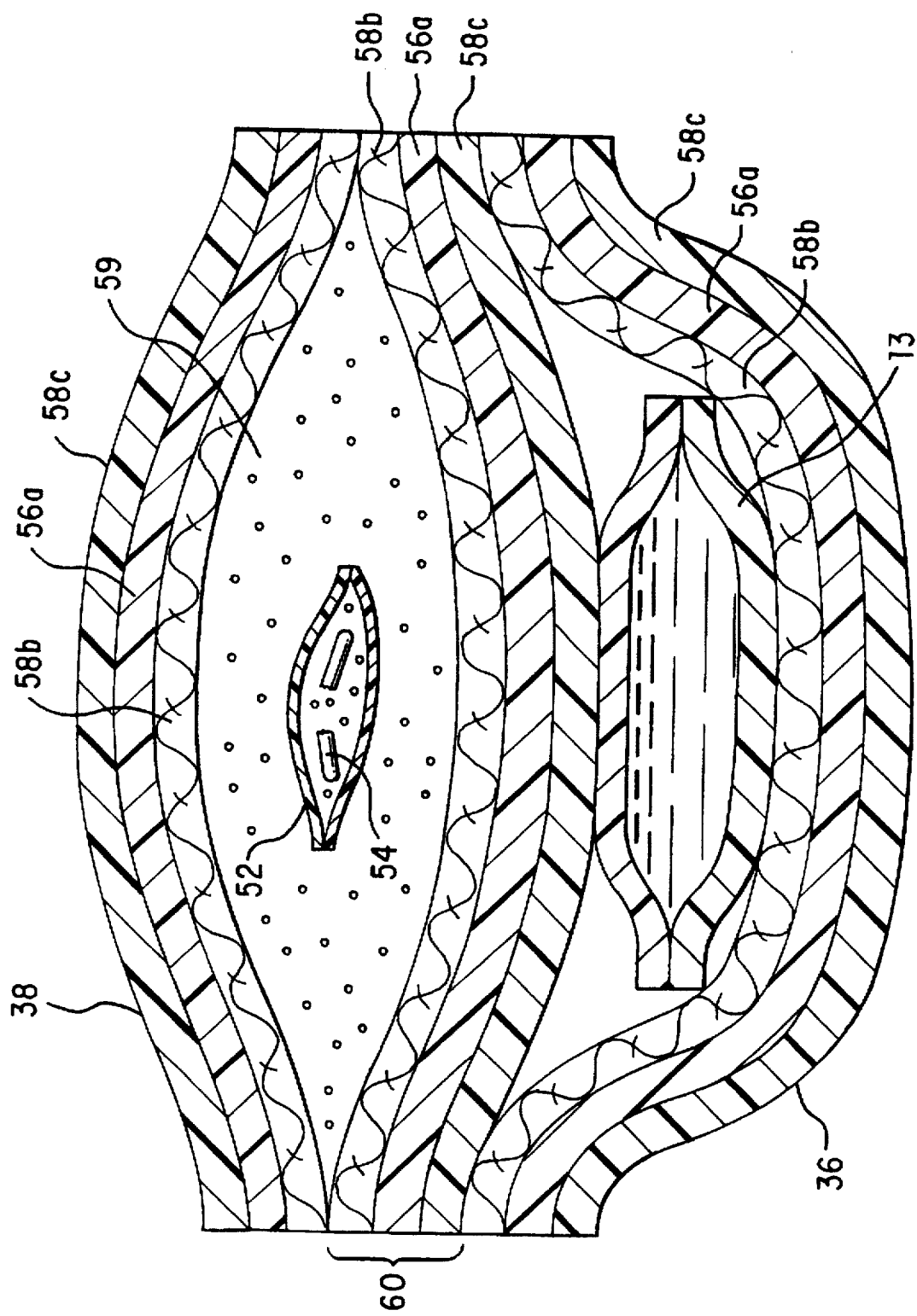
FIG. 12 is a transverse section taken through an inflated sleeve and bladder member after pressurization showing multilayer laminates for the walls of the bladder portion and sleeve portion of the combination sleeve and bladder member.

Another alternative embodiment of barrier means for the bladder portion 38, as best illustrated in FIG. 12, consists of a laminated or coated bladder portion wherein the flexible material of the bladder and barrier means utilizes a single multilayer combination (having at least two layers). As will be understood by one skilled in the art, many combinations of materials are suitable for creating such a multilayer bladder/barrier means. When practicing this embodiment of the instant invention, it is preferred that the materials used to make the multilayer combination are ordered such that the material closest to the gas has the highest material stiffness or elastic modulus, and the materials which can be laminated thereon are successively less stiff. Hence, the material forming the outermost layer, or which is furthest from the gas, has the least material stiffness or elastic modulus. As illustrated in FIG. 12, the barrier layer 56a of polyvinylidene chloride is laminated to the outer surface of layer of fabric reinforced polyurethane 58b and to the inner surface of a layer of non-reinforced polyurethane 58c. For the layers of this flexible plastic, multilayer combination (or laminate) the order of decreasing material stiffness (or increasing elastic modulus) is fabric reinforced polyurethane 58b, polyvinylidene chloride 56a and non-reinforced polyurethane 58c. Thus, as can be seen from FIG. 12, the flexible plastic material of the walls of the bladder portion 38 comprises three laminated layers (of plastic material) of differing material stiffness wherein the layers are arranged, looking in a direction outwardly from the interior 59 of the bladder portion 38, in order of decreasing material stiffness. In other words, the layer of the composite laminate having the greatest material stiffness (or highest elastic modulus) lies closest to the interior 59 of the bladder portion 38.

Likewise, in this alternative embodiment illustrated in FIG. 12, the flexible material of the sleeve portion 36 comprises at least two laminated layers (of plastic material) of differing material stiffness, the layers being arranged, again looking in a direction outwardly from the interior 59 of the bladder portion 38, in order of decreasing material stiffness. Thus, the layer of the composite laminate of at least the wall 60 of the sleeve portion 36 lying closest to the interior 59 of the bladder portion 38 has the greatest material stiffness (or highest elastic modulus).

Figure 6:
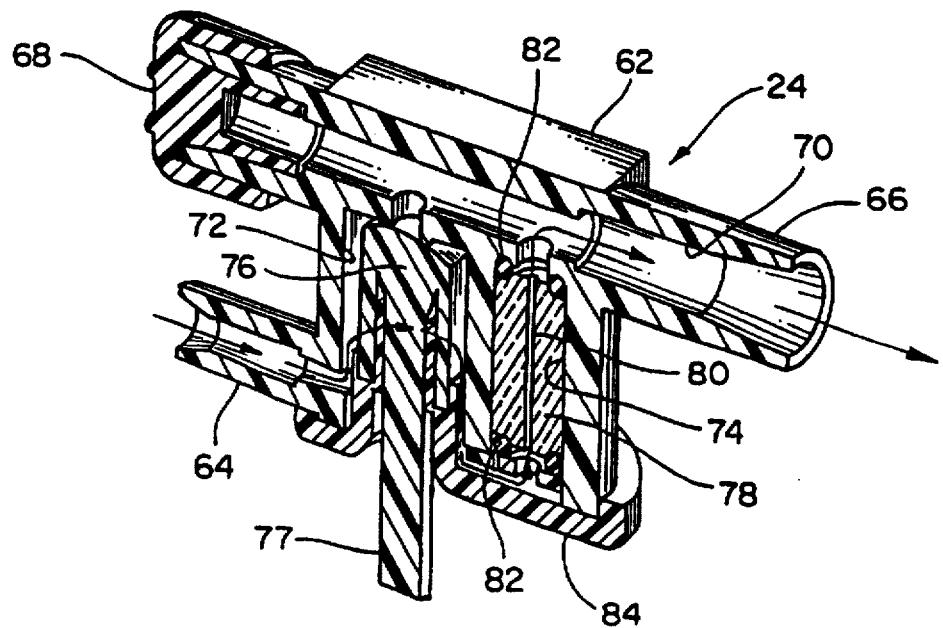
FIG. 6 is an enlarged longitudinal section of a perspective view of the restrictor during normal minimal infusing flow rate of saline solution therethrough.
Figure 7:
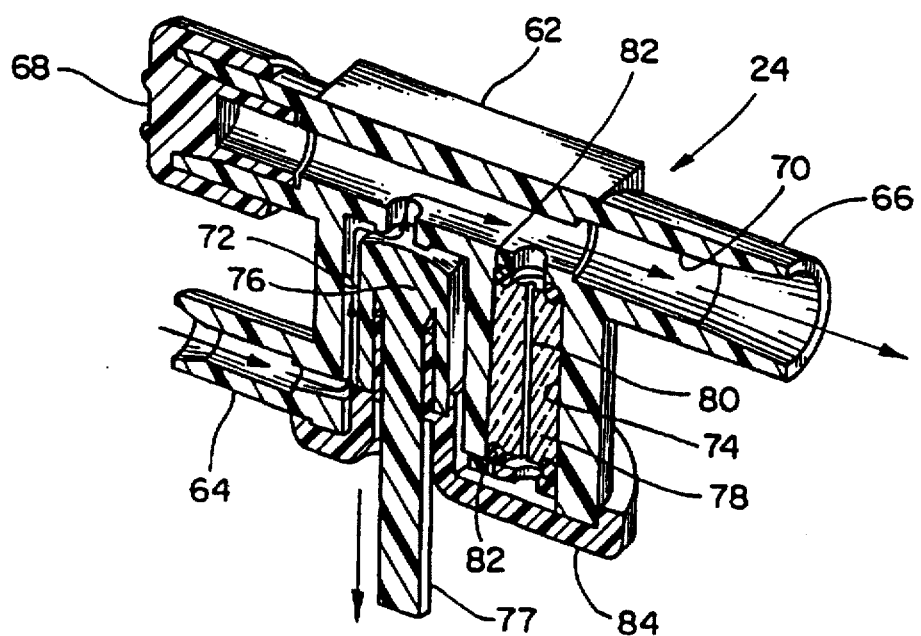
FIG. 7 is a view similar to FIG. 6 with the bypass open, as during a restrictor and indwelling catheter flushing operation.

As shown in FIG. 1, the restrictor 24 which determines the low rate of flow of the saline solution into the patient is located in the tube set 18 at a location adjacent the patient's As best illustrated in FIGS. 6 and 7, the restrictor 24 includes a housing 62 having an inlet port 64 and an offset but parallel outlet port 66, the opposite end of which is closed by a reseal 68 which is in axial alignment with an outlet passage 70 of the outlet port 66. Two parallel passages 72 and 74 are disposed normally to the outlet passage 70 and each is in fluid communication with both the inlet port 64 at one end thereof and the outlet passage 70 at the opposite end thereof. The passage 72 serves as a bypass passage and has a resilient, manually operable valve member 76 disposed therein. Normally, the inner end of the bypass valve 76 is biased into its innermost position blocking the passage therefrom into the outlet passage 70. A glass capillary member 78 having an axial capillary passage 80 of a predetermined size is disposed in passage, 74 and has O-rings 82 sealing opposite ends thereof. A housing cover 84 serves to retain the bypass valve 76 and the capillary member 78 in their respective passages 70 and 72.

During normal KVO (keep vein open) operation of this system, saline solution from the flexible bag 13 if forced through the tube set 18, including the air elimination filter 22, and into the restrictor 24 through the inlet port 64, into the bypass passage 72 and around the closed bypass valve 76 into the capillary passage 74 and through the capillary passage 80 of the glass capillary member 78 into the outlet passage 70 and through the outlet port 66 to the patient's indwelling vein access site.

When the patient requires medication, it may be easily administered through the reseal 68 in the usual manner.

Following each such administration, it is necessary to flush the restrictor outlet passage 70 to ensure that the patient gets the full prescribed dosage of medication. Such flushing also cleans the restrictor and the down stream portions of the tube set 18 in case the next drug to be administered is incompatible with the previously administered drug. The flushing is accomplished by pulling a stem 77 of the bypass valve 76 outwardly whereby the saline solution from the bag 13 flows directly through the bypass passage 72 into the restrictor outlet passage 70, bypassing the capillary member 78, until the bypass valve stem 77 is released and the bypass valve 76 is biased back into its bypass closing position shown in FIG. 6.

It is noted that the reseat 68 is disposed at a right angle to the bypass passage 72 thereby defining a T-shaped configuration which maximizes the flushing effect within the restrictor 24 when the bypass valve 76 is open.

To provide a visual indication as to when the bag 13 of saline solution is approaching empty, the word EMPTY is imprinted on the inner sleeve side wall 32 toward the bottom thereof, as shown at 86 in FIG. 8, which imprint 86 is visible through the outer sleeve side wall 34 only when the two side walls 32 and 34 defining the sleeve portion 36 are fairly close together due to the matte finish of the outer side wall 34. For instance, when a full bag 13 of saline solution is inserted into the sleeve portion 36, the sleeve side walls 32 and 34 are spaced so far apart that the imprint 86 is not visible. However, as the bag 13 empties and collapses, the sleeve side walls 32 and 34 become closer and closer together with the imprint 86 becoming visible as the bag 13 approaches an empty condition.

While there has been shown and described several possible embodiments of the invention, it will be obvious to those skilled in the art that changes and modifications may be made without departing from the invention, and it is intended by the appended claims to cover all such changes and modifications as fall within the true spirit and scope of this invention. For instance, liquid medications such as antibiotics, cancer-treating drugs, etc. may be substituted for the saline solution in the flexible bag 13 whereupon said liquid medication may be continuously infused at a minimal flow rate and at a nearly constant pressure. Moreover, the amounts of chemical components for the gas-generating reactive chemical means may vary. For example, when aqueous citric acid is utilized with excess powdered sodium bicarbonate, generally 40% to 60%, preferably 50% by weight, citric acid is used with from 3.7 grams (g) to 7.0 g of sodium bicarbonate within a generally rectangular gas-permeable sealed packet (moisture-and-debris barrier) having a total surface area of about 10 square inches to generate about 15 pounds per square inch gauge pressure (psig) within a 100 ml bladder portion. Typically enough 50% by weight citric acid is utilized with 7 g of sodium bicarbonate in the aforesaid 10 square inch sealed packet to provide 15 psig pressure in the aforesaid 100 ml bladder portion. Of course, depending on such factors as the size of the bladder portion, the pressure desired and reaction rate for gas-generation desired, the quantities of the components of gas-generating reactive chemical means will vary.

What is claimed is:

1. An ambulatory energized container system for delivering a solution from a flexible bag of solution into a patient's indwelling vein access device, said ambulatory energized container system comprising:

a combination sleeve and bladder member, said combination member having a bladder portion and a sleeve portion, said bladder member comprising first and second sheets of a laminar material, said first and second sheets welded together along a top weld line, said first and second sheets welded together along a bottom weld line substantially parallel to and spaced from said top weld line, said first and second sheets welded together along a first side weld line substantially perpendicular to said top and bottom weld lines, said first and second sheets welded together along a second side weld line substantially parallel to and spaced from said first side weld line, said first and second sheets welded together along a first corner weld line, said first corner weld line intersecting said top weld line and said first side weld line at substantially 135° angles, said first and second sheets welded together along a second corner weld line, said second corner weld line intersecting said top weld line and said second side weld line at substantially 135° angles, said first and second sheets welded together along a third corner weld line, said third corner weld line intersecting said bottom weld line and said second side weld line at substantially 135° angles; and said first and second sheets welded together along a fourth corner weld line intersecting said bottom weld line and said first side weld line at substantially 135° angles;

gas-generating means disposed within said bladder portion, said gas-generating means comprising a first reactive composition, a second reactive composition, and a segregating means for segregating said first and second reactive compositions, said segregating means being openable by manual manipulation thereof resulting in an exposure of said first reactive composition to said second reactive composition, said first and second reactive compositions being selected such that exposure of said first reactive, composition to said second reactive composition produces a chemical reaction resulting in a formation of a volume of gas sufficient to expand said bladder portion.

2. An ambulatory energized container system in accordance with claim 1, wherein said laminar material comprises a plurality of lamina of varying elastic moduli, said plurality of lamina arranged in order of decreasing elastic moduli from an interior of said bladder member to an exterior of said bladder member.

3. An ambulatory energized container system for delivering a solution from a flexible bag into a patient's indwelling vein access device, said ambulatory energized container system comprising:

a combination sleeve and bladder member, said combination member having a bladder portion and a sleeve portion, said bladder portion comprising a laminar material having a plurality of lamina of varying elastic moduli, said plurality of lamina arranged in order of decreasing elastic moduli from an interior of said bladder member to an exterior of said bladder member, said sleeve portion being constructed of a flexible material and being capable of receiving therein a flexible container for solution in a position in said sleeve portion alongside said bladder portion of said combination member, gas-generating means disposed within said bladder portion, said gas-generating means comprising a first reactive composition, a second reactive composition, and a segregating means for segregating said first and second reactive compositions, said segregating means being openable by manual manipulation thereof resulting in an exposure of said first reactive composition to said second reactive composition, said first and second reactive compositions being selected such that exposure of said first reactive composition to said second reactive composition produces a chemical reaction resulting in a formation of a volume of gas sufficient to expand said bladder portion.

4. The ambulatory energized container system of claim 3, wherein said gas-generating means is disposed within a barrier means for retaining moisture and debris, and wherein said barrier means for retaining moisture and debris is disposed within said bladder portion of said combination member.

5. The ambulatory energized container system of claim 3, wherein said gas-generating means contains quantities of said first and second reactive compositions sufficient to exert a pressure on said flexible bag for solution for at least 2 hours.

6. The ambulatory energized container system of claim 3, wherein said laminar material comprises an inner layer constructed of a fabric-reinforced polyurethane material, an intermediate, barrier layer constructed of a polyvinylidene chloride material, and an outer layer constructed of a non-reinforced polyurethane material.

7. The ambulatory energized container system of claim 3 wherein said system further comprises a means for signalling an empty condition of said flexible container, said means for signalling comprising an indicia on said sleeve portion of said combination bladder and sleeve member.

8. The ambulatory energized container system of claim 3, wherein said first reactive composition comprises sodium bicarbonate and wherein said second reactive composition comprises citric acid.

9. The ambulatory energized container system of claim 8, wherein said segregating means for segregating said gas-generating reactive chemical means comprises a frangible ampoule, and wherein one of said first and second reactive compositions is disposed within said frangible ampoule and the other of said first and second reactive compositions is disposed outside said frangible ampoule.

* * * * *